United States Patent
Robertson, Jr.

(10) Patent No.: US 7,468,029 B1
(45) Date of Patent: Dec. 23, 2008

(54) PROGRESSIVE BIVENTRICULAR DIASTOLIC SUPPORT DEVICE

(76) Inventor: Abel L. Robertson, Jr., P.O. Box 3125, Half Moon Bay, CA (US) 94019

( * ) Notice: Subject to any disclaimer, the term of this patent is extended or adjusted under 35 U.S.C. 154(b) by 254 days.

(21) Appl. No.: 10/163,159

(22) Filed: Jun. 4, 2002

Related U.S. Application Data

(60) Provisional application No. 60/295,912, filed on Jun. 4, 2001.

(51) Int. Cl.
*A61F 13/00* (2006.01)
(52) U.S. Cl. .......................... 600/37; 600/16
(58) Field of Classification Search ............ 600/16–18, 600/37; 623/3.1, 3.16, 3.17, 3.21, 3.29; 128/897; 601/151–153
See application file for complete search history.

(56) References Cited

U.S. PATENT DOCUMENTS

| | | | | |
|---|---|---|---|---|
| 4,957,477 A | * | 9/1990 | Lundback | 600/16 |
| 5,169,381 A | * | 12/1992 | Snyders | 600/16 |
| 5,256,132 A | * | 10/1993 | Snyders | 600/16 |
| 5,749,839 A | * | 5/1998 | Kovacs | 601/153 |
| 6,432,039 B1 | * | 8/2002 | Wardle | 600/37 |

* cited by examiner

*Primary Examiner*—John P Lacyk
(74) *Attorney, Agent, or Firm*—James J. Leary; Carol D. Titus

(57) ABSTRACT

A device is proposed to progressively reduce the hemodynamic cardiac symptoms of congestive heart failure as well as those induced by dilated cardiomyopathies. This device affords progressive diastolic ventricular control by offering a method for percutaneous access and adjustments of its gas filled bladders surrounding the heart. After opening the pericardium, the device is not attached to the heart muscle but may be anchored to the pericardial sac. The device actually extends primarily around the heart from below the atrioventricular canal to the cardiac apex. Between the device exterior, made of non-elastic material and the epicardium, two independent elastic bladders or chambers provide variable compressive diastolic support to the right and left ventricles, while allowing adequate blood flow to the anterior and posterior descending epicardial branches of the coronary arteries and veins. Progressive hemodynamic increases in diastolic pressures for the right and left ventricles can be individually and repeatedly monitored by pressure gauges and an inert gas separately injected or removed in the enclosed chest through self-sealing access ports. These ports are subcutaneously implanted in the left anterior axillary line and connected by thin tubes across the 4th or 5th intercostal spaces to the pericardial bladders or chambers described above.

20 Claims, 14 Drawing Sheets

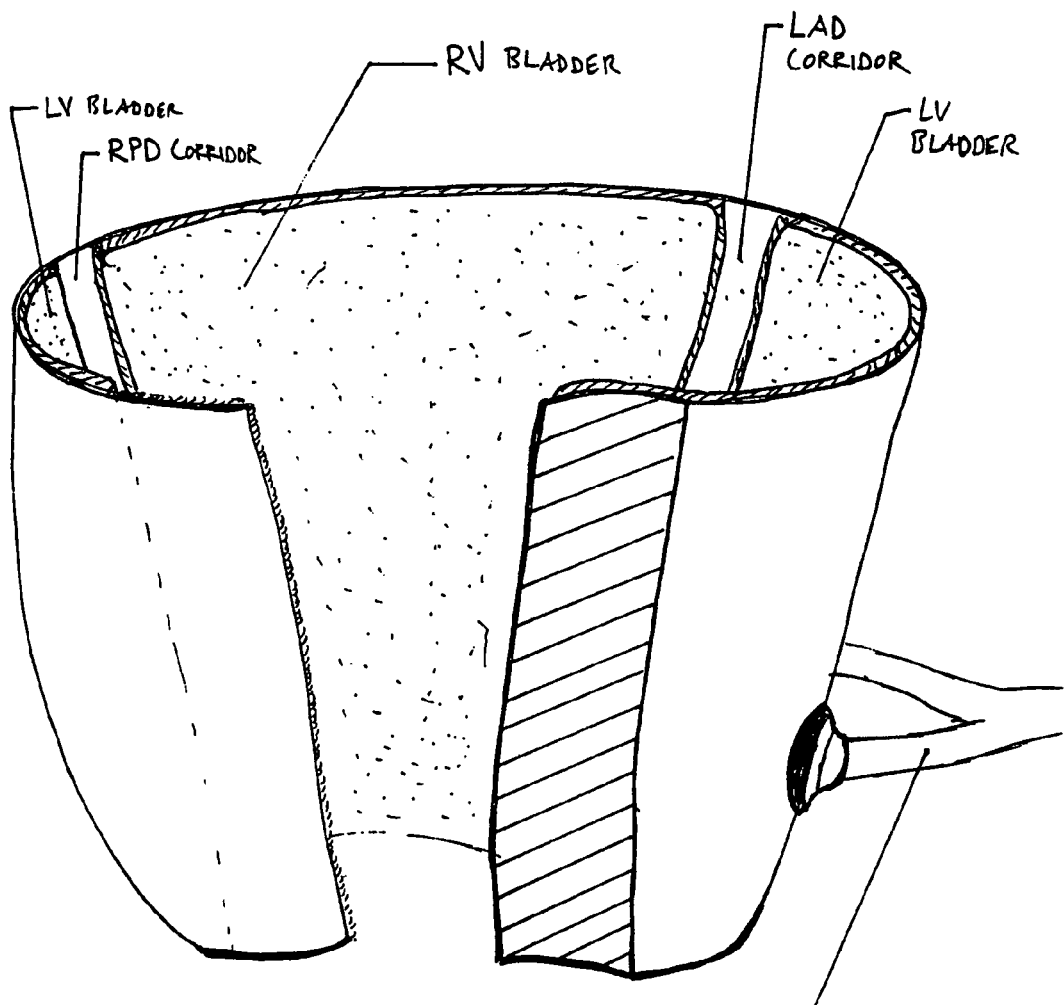
FIG 1
 SEALING/CLOSURE ZONE
 BLADDERS

CLOSURE SYSTEMS FOR PROGRESSIVE BIVENTRICULAR DIASTOLIC ASSIST

Hook & Loop Strip

Lacing System

Sewn/Sutured Together

STRAPS W/ CLIPS

BELT & PEGS

* CATHETER PORT ENABLES CATHETER ACCESS TO HEART FOR DIAGNOSTIC OR THERAPEUTIC USE

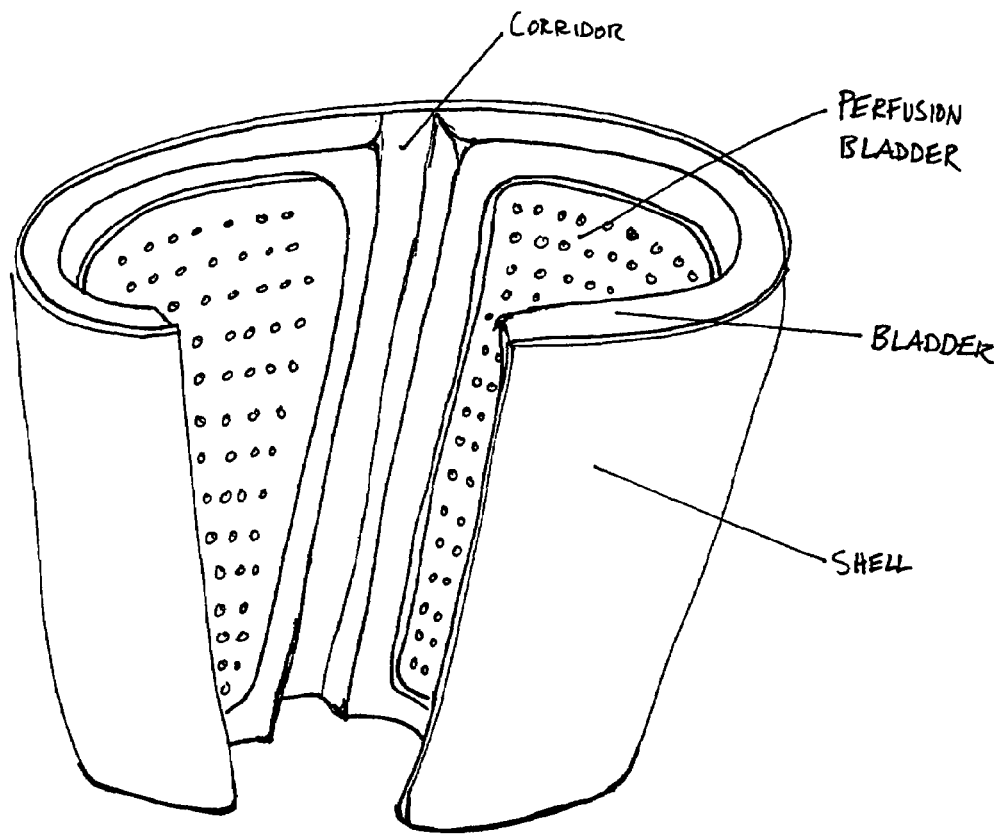
FIG 13A
FIG 13B
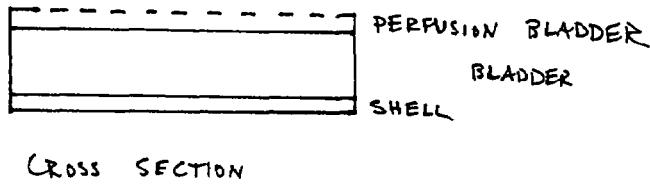
Cross Section

PROGRESSIVE BIVENTRICULAR DIASTOLIC SUPPORT DEVICE

CROSS REFERENCE TO OTHER APPLICATIONS

This application claims the benefit of U.S. provisional patent application No. 60/295,912, filed Jun. 4, 2001. This and all other US patents and patent applications referred to herein are hereby incorporated by reference.

FIELD OF THE INVENTION

The present invention relates to the need for progressive treatment of a variety of clinical conditions resulting in cardiac failure.

BACKGROUND OF THE INVENTION

Congestive heart failure and dilated cardiomyopathies are just two conditions that result in the elongation of individual myocytes. The resulting hemodynamic disadvantages of significant ventricular dilatation (either right or left) can be overcome by progressive epicardial compression resulting in reduction of diastolic ventricular volume, increased ventricular contractility and improved cardiac output. Research has also shown that regression of fibrosis and hypertrophy occurs when loading is reduced on a failing heart (Bruckner, et al., 2001).

Patients that will receive particular benefit are those suffering from non-ischemic cardiomyopathy. These cases can be further stratified into dilated, hypertrophic and restrictive cardiomyopathy. The three classes describe differing muscle damage to the heart. The most common type is dilated cardiomyopathy. Myocytes are stretched due to some mechanism such as disease or increased workload. The elongated or hypertrophic myocytes lead to a dilated ventricle (either right or left). In what may be a misguided attempt to compensate for this state, such a heart will allow itself to become further stretched, inducing secondary focal ischemia, which in fact leads to further degradation of the heart's ability to perform (Robertson, 1999). Heart failure is the hallmark of dilated cardiomyopathy.

The inventor has studied the cellular physiology involved in compensation. In particular, the mechanisms of vasoconstriction, increased cardiac adrenergic drive, and the activation of transcription factors and their short term and long term implications that produce heart failure (Robertson). Also, compressive mechanical support of a dilated heart has been shown to reduce the cardiac workload. In a study using ventricular assist devices, reduced cardiac workload has shown regression of heart failure symptoms. Therefore, compressive mechanical support will reduce the condition of heart failure. Progressive control will afford optional recovery for an individual patient. In earlier research related to the treatment of arterial aneurysms, the idea of a progressive therapeutic support mechanism had shown clinical relevance in studies on animal models decades ago. With an understanding of the pathophysiology of congestive heart failure and of cardiomyopathy this approach is directly needed for safe and cost-effective treatment of the failing heart.

The device can be thought of in two parts. First, a cardiac enclosure affords a means of defining an upper limit on the cardiac geometry. This geometry can subsequently be adjusted through two or more highly elastic and/or highly conforming chambers or bladders that reside on the inside of the enclosure. The independent inflation of each chamber addresses the needs for specific progressive support of the individual ventricular diastolic volume. For example, in the case of congestive heart failure usually the right ventricle is predominantly dilated, inducing higher diastolic systemic pressure while not initially changing the geometry of the left ventricle to a substantial degree. In contrast, in left ventricular failure, usually following transmural myocardial infarction, or in dilated cardiomyopathies, progressive support is required for the left cardiac chamber to reduce ventricular volume. Eventually, in many cases, both ventricles may become dilated and require support.

At present no publications address the need for an easily adjustable, percutaneous, gas/liquid filled cardiac support device. Previous experimental and anatomopathological studies by the inventor have suggested the potential reversibility of heart failure by reducing elongation of individual ventricular myocardial fibers. This may also reduce the incidence of randomized programmed cell death or apoptosis and reverse losses of ventricular contractility.

In summary, the treatment of congestive heart failure and dilated cardiomyopathies, which involves over 500,000 new cases a year, in the U.S. alone, could be strongly impacted by such a device. It offers to the cardiothoracic surgeon the use of a customized progressive ventricular diastolic assist device requiring no external mechanical support, while allowing repeated percutaneous adjustments based on clinical and hemodynamic data that provides a novel solution to a large patient population.

DESCRIPTION OF THE PRIOR ART

The following patents and publications describe technology related to the treatment of cardiomyopathy:

U.S. Pat. No. 5,800,528 Lederman et al. Passive girdle for heart ventricle for therapeutic aid to patients having ventricular dilatation U.S. Pat. No. 5,848,962 Feindt et al. Device for assisting cardiac function U.S. Pat. No. 5,908,378 Kovacs & Lowe Bi-ventricular cardiac assist device U.S. Pat. No. 5,971,910 Tsitlik, et al. Method and apparatus for assisting a heart to pump blood by applying substantially uniform pressure to the ventricles U.S. Pat. No. 6,165,121 Alferness Cardiac reinforcement device U.S. Pat. No. 6,165,122 Alferness Cardiac reinforcement device WO 0036995 Wardle Method and apparatus for reinforcement of the heart ventricles (U.S. patent application Ser. No. 09/346,643, filed Jul. 1, 1999.)

OTHER PUBLICATIONS

Artrip, J. H. et al., "Maximizing hemodynamic effectiveness of biventricular assist by direct cardiac compression: a study in ex vivo and in vivo canine models of acute heart failure". J Thorac CarioVasc Surg 120(2) 379-86, 2000.

Bruckner, B. A. et al., "Regression of fibrosis and hypertrophy in failing myocardium following mechanical circulatory support". J Heart Lung Transplant. 20(4) 457-464, 2001.

Power, J. M. et al., "Passive ventricular constraint amends the course of heart failure: a study in an ovine model of dilated cardiomyopathy". Cardiovascular Research 44(3)549-555 1999.

Robertson, Jr. A. L., "Cellular changes in Heart Failure". Resident and Staff Physician 45(4) 10-24, 1999.

Sabbah (A), H. N. et al., "Chronic therapy with the acorn cardiac support device in dogs with chronic heart failure: three and six month hemodynamic, histologic and ultrastructural findings". J Heart and Lung Transplant 20(2) 189, 2001.

Sabbah (B), N. H. et al., "Efficacy trends of the acorn cardiac support device in patients with heart failure: a one year follow-up". J Heart Lung Transplant 20(2) 217, 2001.

At present, efforts to restrain the heart from further dilation have shown clinical relevance (Power et al., 1999). Patents by Acorn Cardiovascular (U.S. Pat. No. 6,165,121 & U.S. Pat. No. 6,165,122) have specifically addressed the need for a solution that restrains the ventricular geometry of patients with heart failure or cardiomyopathy. They have disclosed the use of a cardiac reinforcement device (CRD) made of an "intricate knit of multifilament polyester yarn". Limitations of the Acorn device include 1) the need in the Acorn system to surgically adjust the jacket and 2) no differential constraints between the two ventricles is provided.

Direct cardiac compensation significantly has been shown to reduce end-diastolic pressure while increasing cardiac output to about 60% of normal in the setting of acute heart failure (Artrip et al., 2000).

Published studies of experimental findings using the commercial CRD have shown that a layer of fibrosis forms (Sabbah (A & B), et al., 2001). It is known that fibrosis reduces the contractility of cardiac muscle.

Lederman et al., (U.S. Pat. No. 5,800,528) disclosed a device that is a girdle that may be adjusted over time for mechanical restraint of the heart. Their invention identifies only one system by which adjustment is to take place. They describe, in their FIG. 3, that an "electronic actuator 22 controls a conventional mechanical fluid actuator which provides for increase and decrease of fluid within the girdle." This invention discloses no other means by which the girdle may be filled with fluids and thus does not enable it to be built except with the previously noted actuators. This system is still unclear as to whether the controlling/filling device is implanted or not as well. As an implant this may seriously jeopardize care and in the case where the device is external it involves some open transition to a console which also reduces patient mobility and increase risk of infection.

Kovacs & Lowe (U.S. Pat. No. 5,908,378) have a ventricular assist activation cuff system that includes bladders about the heart for fitting the heart. Their device has self-sealing bladders that terminate on the exterior of the device. This self-sealing port can then be adjusted only at the time of placement or through a secondary procedure. The nature of the device is also considerably different since it is intended for directly and mechanically assist the ventricles of the heart.

In the physiopathology of the function of cardiac muscles, it has been shown that as ventricular dilatation ensues, there is a marked reduction on the individual cell contractility with significant reductions in cardiac output that the progressive biventricular diastolic assist is designed to prevent.

Some devices such as Feindt et al., (U.S. Pat. No. 5,848,962) are active systems for active pneumatic support that includes controllers to synchronize the device to the heart rate. The level of complexity in this device loses sight of the physiologic need for patients with healthy myocytes. The Feindt, et al., device targets patients with a particularly failing cardiac cycle function, these patients may not be good candidates for the present invention. Similar to Feindt et al., is the invention disclosed by Tsitlik, et al., (U.S. Pat. No. 5,971,910) which offers a large mechanically active support that includes two fluid filled chambers. These chambers are then driven as a part of the cardiac cycle. Tsitlik et al., further state that during diastole there is no support of the heart. This does not address the potential continued dilation of the heart. It is absolutely necessary to offer the patient support during diastole in those patients who have the potential for recovery of their own healthy cardiac output.

This device is not intended to offer support as previously described in the art as being in a feedback loop where adjustment are made during each cardiac cycle. Such a level of complexity offers substantial risk and cost factors that preclude broad adoption within the surgical venue.

Wardle (WO 0036995) describes a device for treating cardiomyopathy, which has a compliant containment structure that surrounds and encases the heart and two or more inflation pockets fabricated from a non-elastic compliant material disposed on the interior surface of the containment structure to support the external wall of at least one of the ventricles of the heart.

SUMMARY OF THE INVENTION

The present invention encompasses the clinical needs for many patients with a number of cardiac conditions. It is a therapeutic treatment device that progressively treats conditions that need ventricular support. The device encloses the heart in such a way that it is geometrically constrained. The enclosure also provides between its inner surface and the epicardium at least one elastic inflatable bladder. Such bladders are initially inflated to conform to the individual patient's particular heart shape. Also provided is a region that does not get inflated to protect the main epicardial coronary branches, the left anterior descending and right posterior descending arteries, from impingement and associated ventricular ischemia. Reduction of any blood flow would likely increase the risk of ischemically developed fibrosis. Preferably, there will be one bladder for each ventricle. Each individual bladder will have an extension in communication with tubing that traverses to a location just below the skin. At the subcutaneously located end of the tubing reside self-sealing injectable ports through which each individual bladder can be adjusted with either more or less pressure via the tubing. This provides the clinician with a percutaneous access site for the progressive adjustment of the ventricular end-diastolic volume.

The multi-lumen enclosure may be manufactured out of a non-elastic but pliable fabric that will conform to the external geometry to the heart. The bladders may be made of an elastic biocompatible material.

The tubing could be constructed of either a continual piece or perhaps a specific catheter attachment system separate from the enclosure. There could be separate tubes for each inflatable bladder, each with a separate self-sealing injection port. In another embodiment, there could be several lumens in a single extruded flexible shaft. The function of this catheter assembly is to provide a convenient fluidic communication pathway that affords easy clinical access. This improves patient morbidity and acceptance by freeing them from external devices/transducers. The assembly that affords the percutaneous adjustment is a novel contribution to the field.

BRIEF DESCRIPTION OF THE DRAWINGS

FIG. 1 is a view of one embodiment of the enclosure. This figure includes a sealing/closure zone, a right posterior descending (RPD) corridor and a left anterior descending (LAD) corridor and bladders for both ventricles. The communication tubes are also disclosed.

FIG. 13A shows the perfusion bladder that is a means for introducing a diagnostic or therapeutic agent to the exterior surface of the heart.

FIG. 13B shows a cross section of the wall of the perfusion bladder of FIG. 13A.

DETAILED DESCRIPTION OF THE INVENTION

Figure 2:
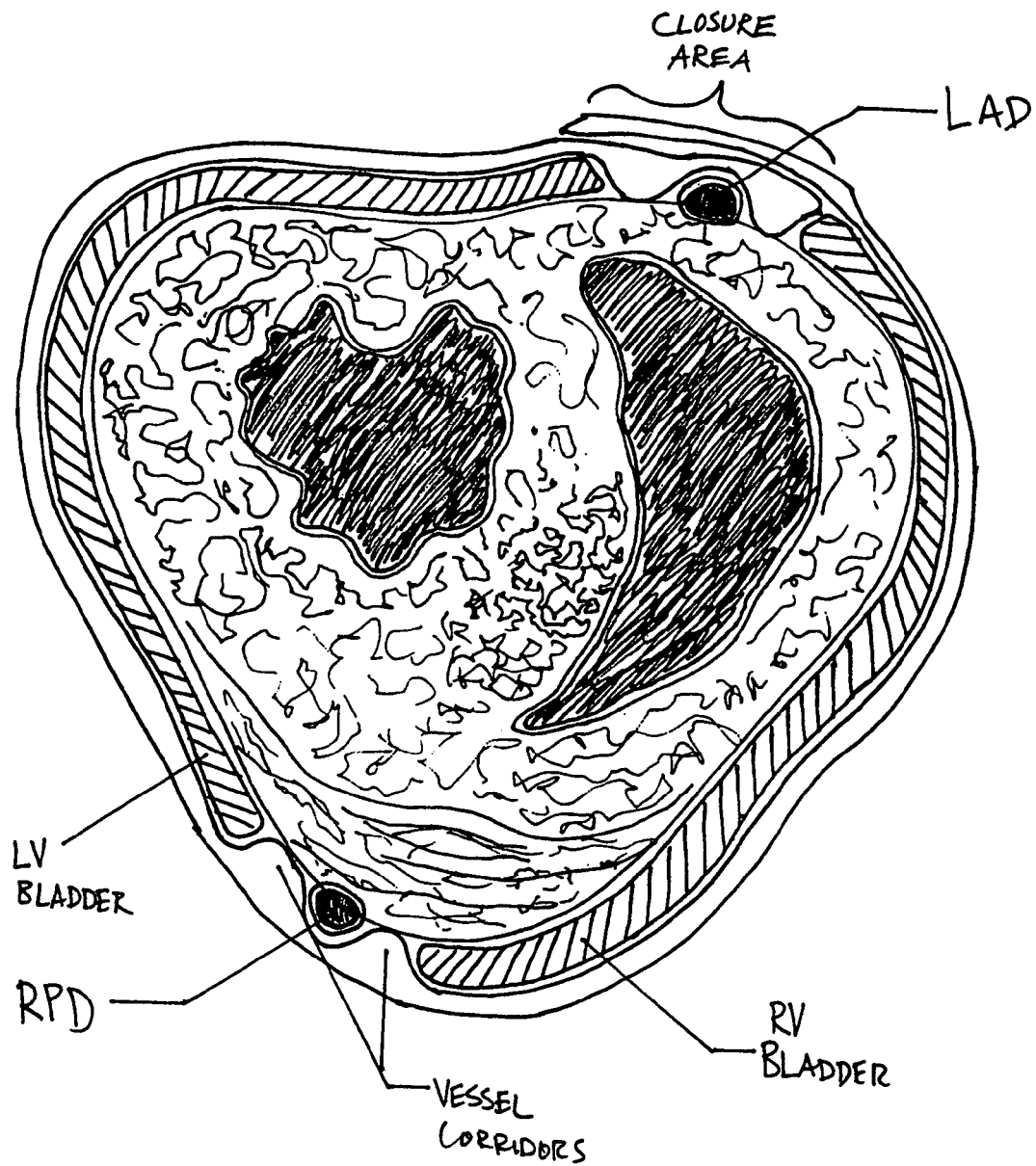
FIG. 2 is a cross-sectional view of the heart to be treated with the closure area, vessel corridor and bladders highlighted. The closure area is located at the LAD for registration purposes.
Figure 3:
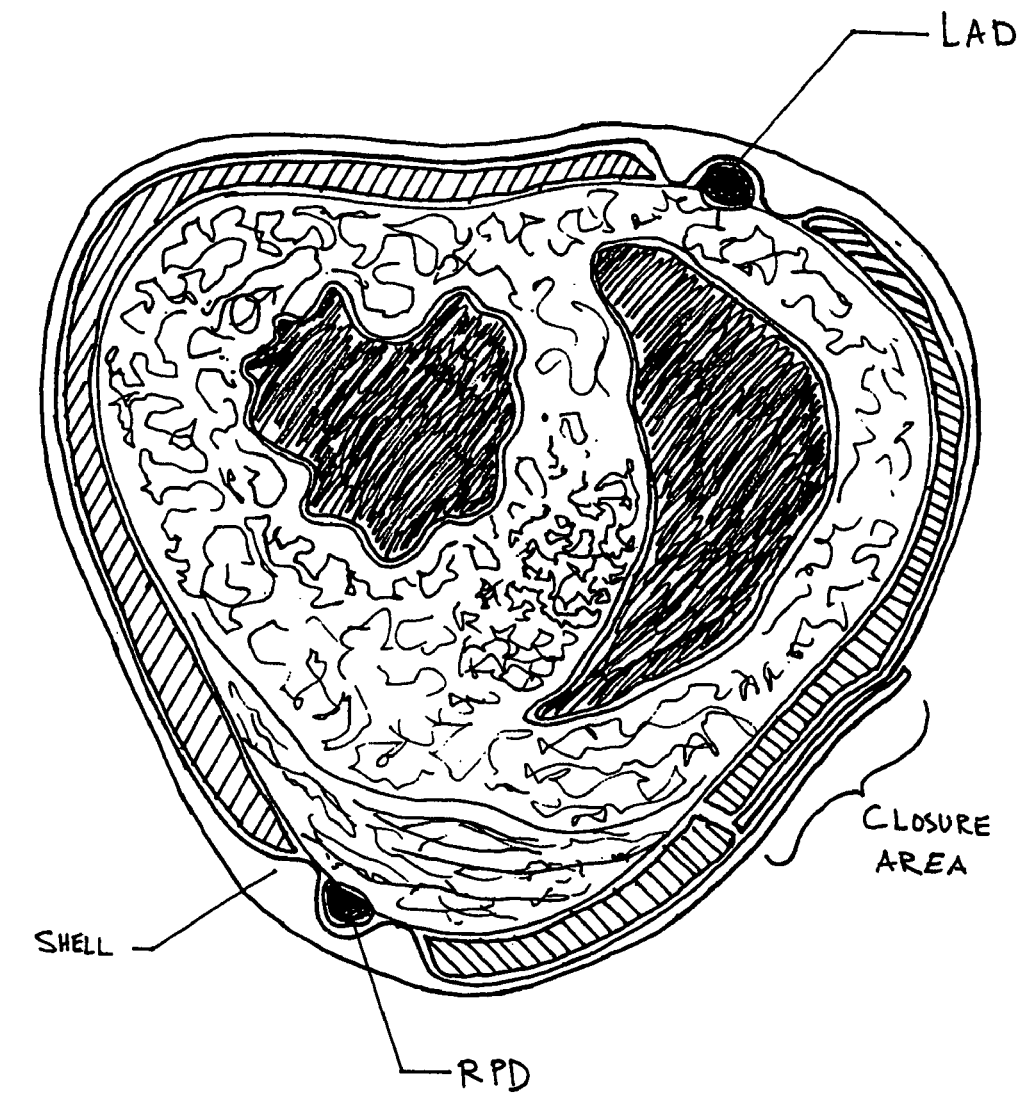
FIG. 3 is also a cross-sectional view with a shell on the exterior. A closure area is also presented, distinct from the LAD area.
Figure 4:
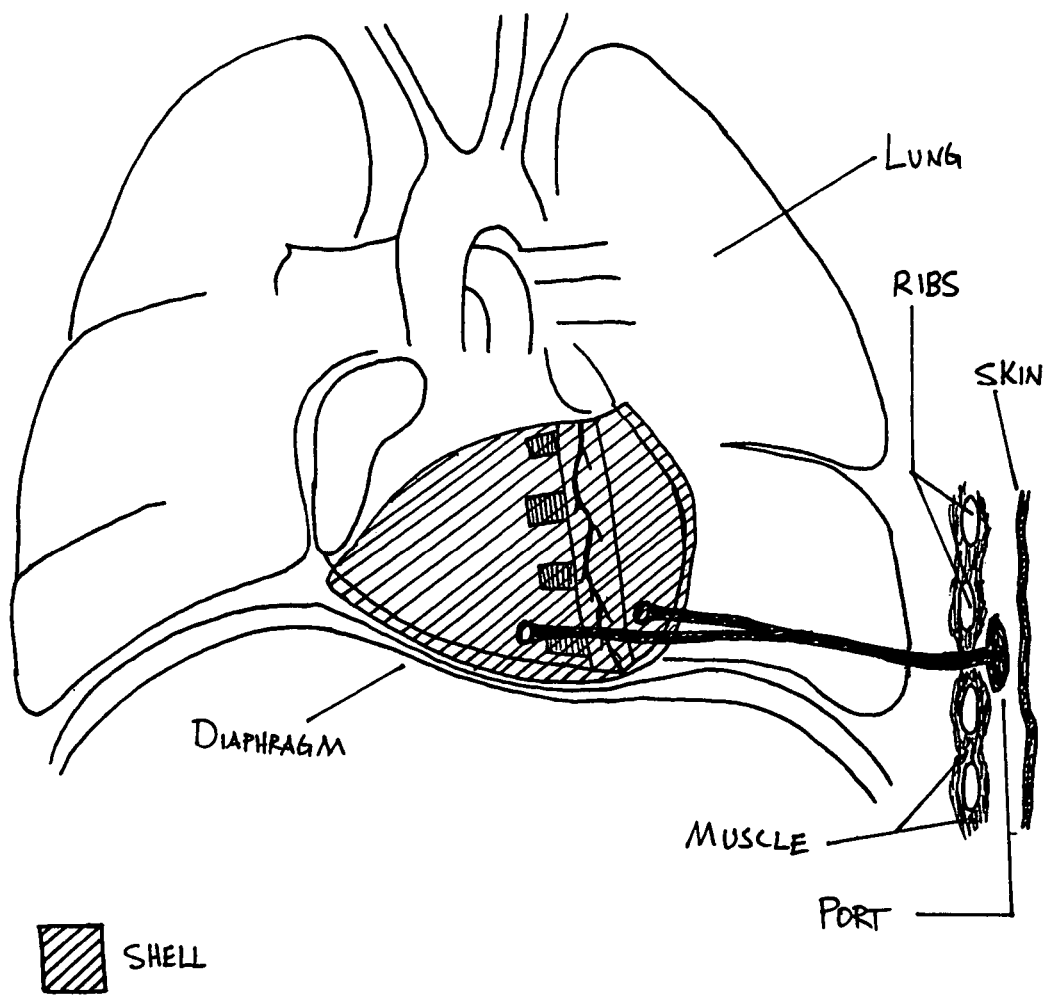
FIG. 4 shows a slice in the frontal plane of the device situated with respect to the lungs and with the communication ports extending to their resident position.
Figure 5:
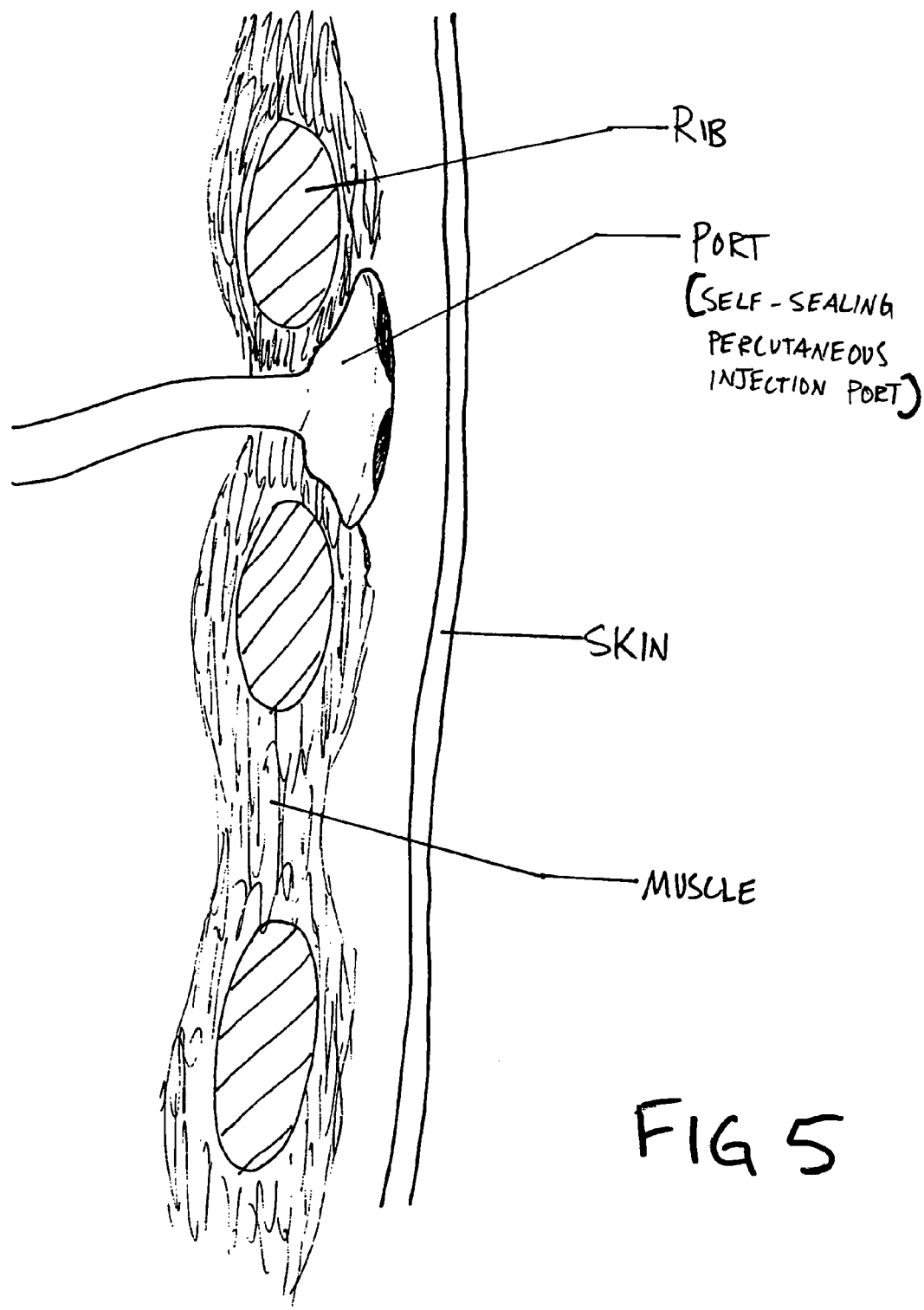
FIG. 5 is a close-up of a self-sealing injection port situated between the ribs.
Figure 6:
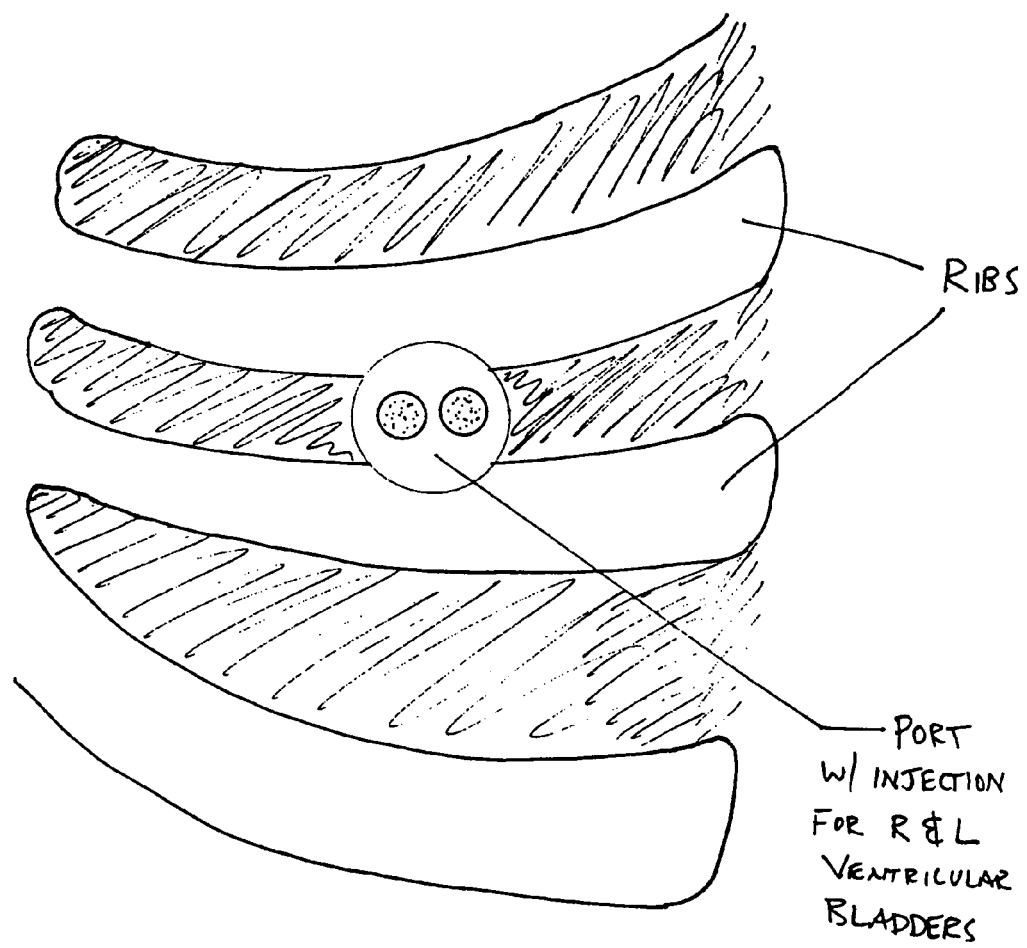
FIG. 6 shows a view of the port in reference to the ribs in the background.
Figure 7:
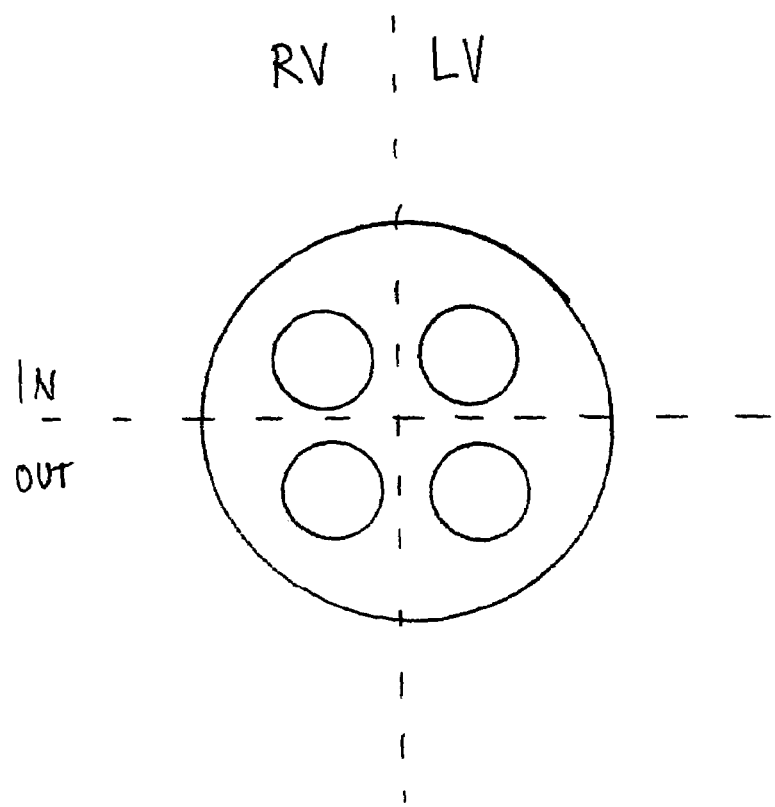
FIG. 7 shows a configuration for temporary thermal management. The in ports introduce fluid or gas into the bladder while a second lumen extracts the resident fluid or gas. This system avoids loss of support or excessive restraint on the heart.
Figure 8A:
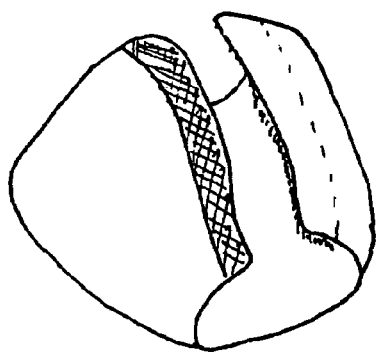
FIGS. 8A-8C show closure systems including hook and loop, lacing of suturing, straps with clips and belt and pegs.
Figure 8B:
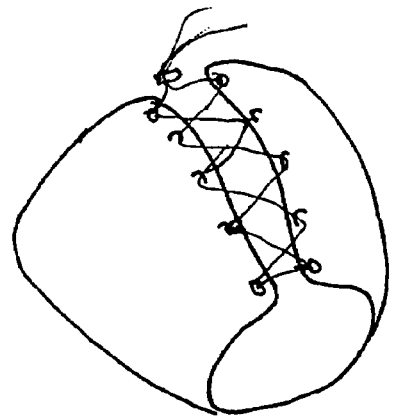
Figure 8C:
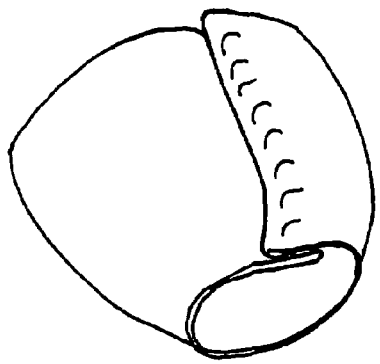
Figure 9A:
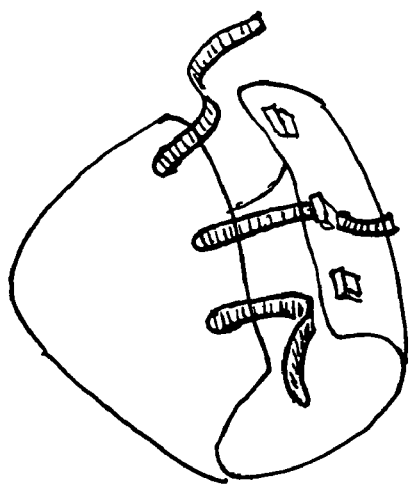
FIGS. 9A-9B show closure systems including hook and loop, lacing of suturing, straps with clips and belt and pegs.
Figure 9B:
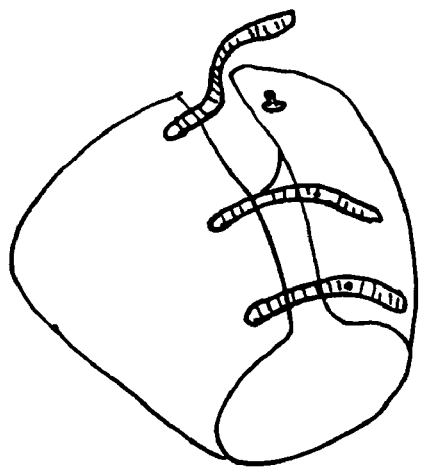
Figure 10:
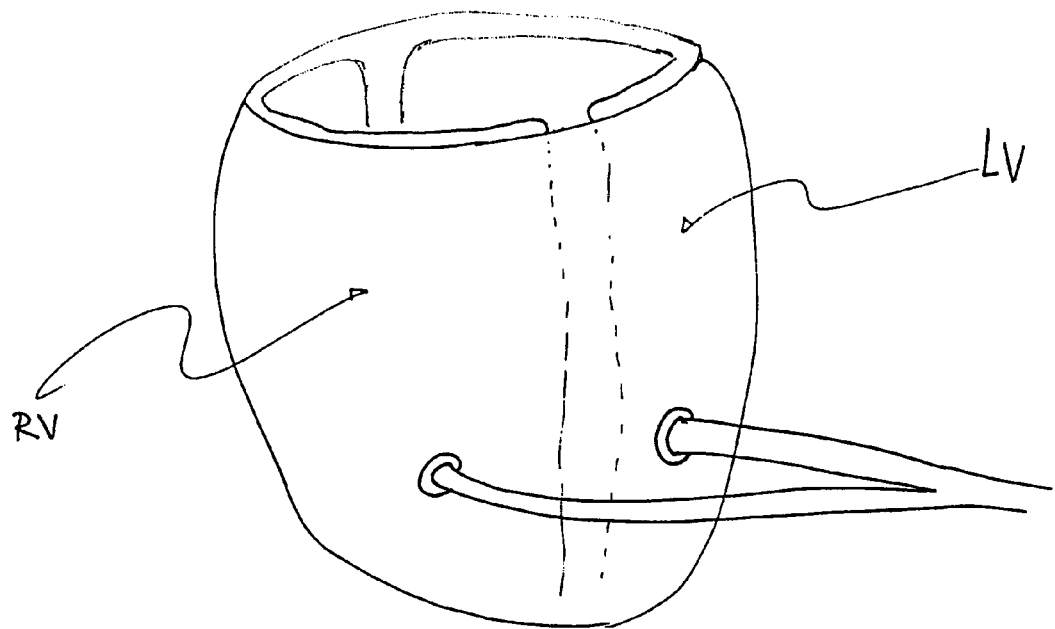
FIG. 10 shows the enclosure in form with bladders and ports for each ventricle.
Figure 11:
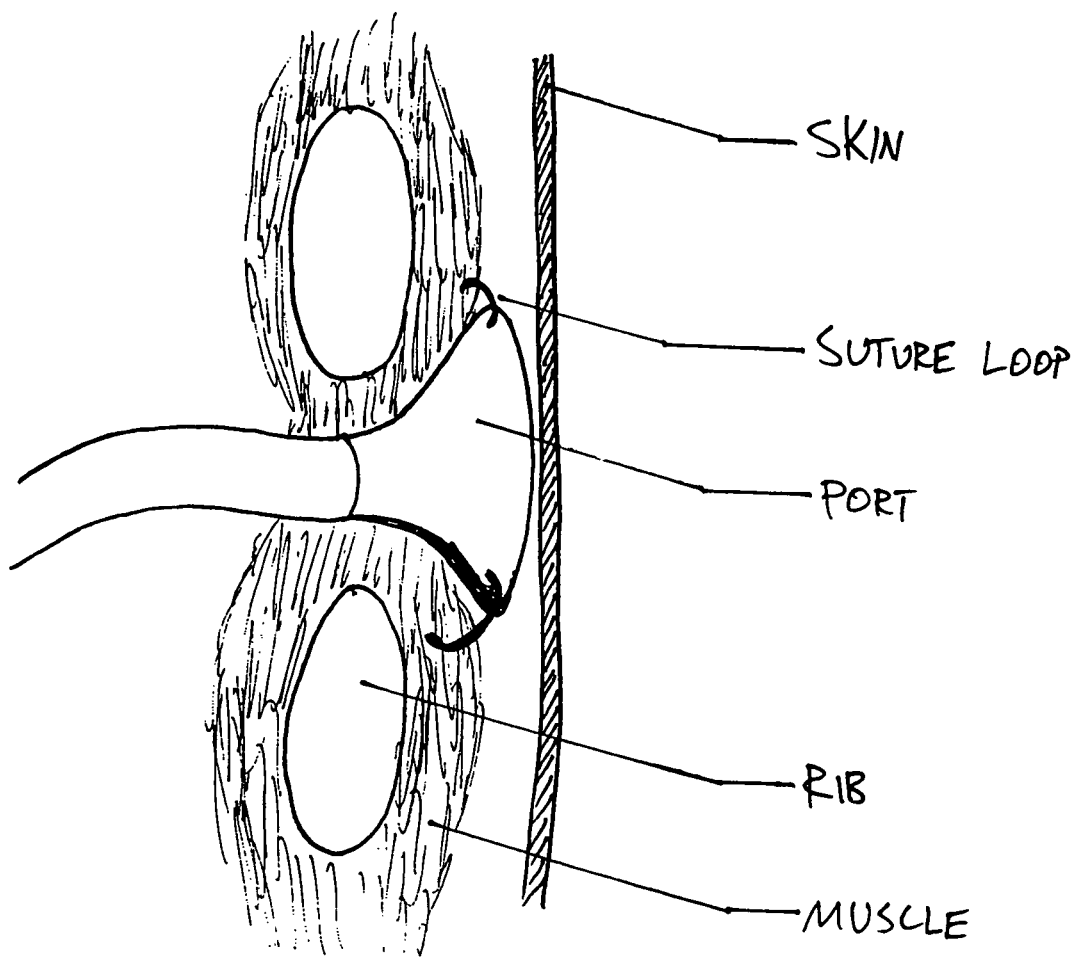
FIG. 11 is a close-up of a self-sealing injection port situated between the ribs. A pair of eyelets are also shown where sutures can be passed to help register the port.
Figure 12:
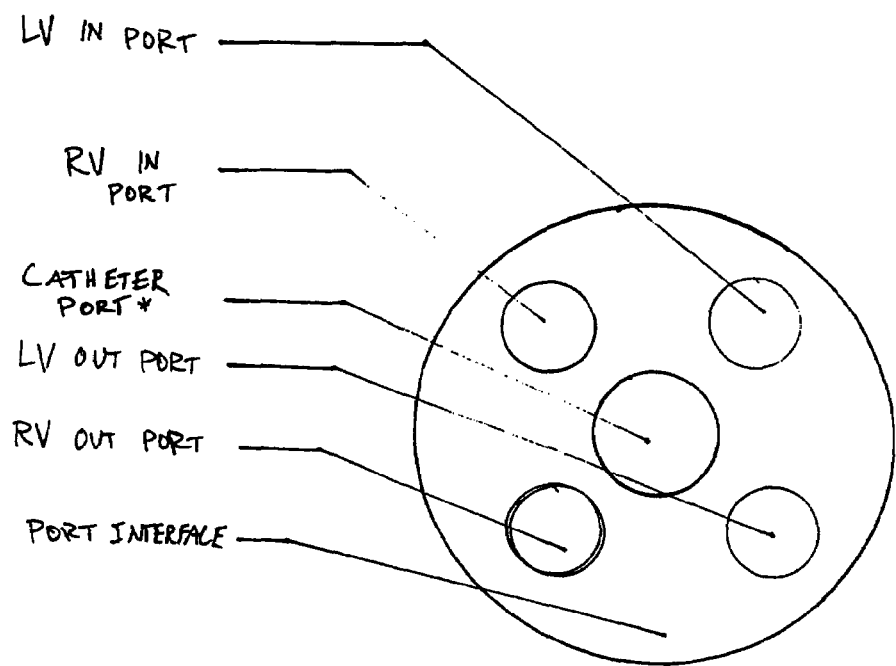
FIG. 12 shows a communication port that offers percutaneous access to the heart for diagnostic of therapeutic use.

In one specific embodiment of the invention, shown in FIGS. 1-12, a left-side thoracotomy approach is followed by opening the pericardial sac to expose the heart. The outward fabric enclosure, modeled from the "human fit" trials is made of a non-elastic material that is slipped over the heart with the apex inserted first. The enclosure has the internal right and left bladders already attached to the side of the enclosure facing the epicardium. Care is taken to note that the seams associated with the binding of the individual bladders maintain a region that protects the epicardial descending coronary arteries from being impinged by the bladders. With the enclosure properly aligned, the enclosure is closed with one or more fasteners, such as hook-and-loop fasteners, in the form of straps or strips. Once the surgeon is satisfied with the enclosure fit including registration of the biventricular canal sutures may be run from the enclosure to the pericardium for fixation. Each bladder may then be individually filled with gas, such as carbon dioxide, through the self-sealing port to produce an initial fit.

The bladders are individually filled with gas delivered through the self-sealing ports using a small gauge needle. With the enclosure and bladders filled to satisfaction, the self-sealing ports must be secured outside the chest cavity in the subcutaneous panniculus along the left anterior axillary line. Skin markings can be made to indicate the location of the ports for right and left ventricles to simplify post-operative adjustments of the bladder volumes.

Once the chest is closed, cardiac function can be monitored to determine the optimal initial setting to initiate recovery of ventricular function. Cardiac output is a strong measure of response, which can be acquired using any of a number of established clinical methods. Cardiac function should stabilize shortly thereafter and further progressive adjustments, on perhaps a weekly basis, may be performed by using small gauge needles to the access ports that provide fluid communication to the bladders.

In further embodiments, the device may be inserted and positioned initially through a series of minimally invasive approaches. In a further embodiment a plurality of chambers may be used to give a conforming custom progressive support. Such a case may involve a region of infarction or of a ventricular aneurysm. Further embodiments may use a series of communication lumens positioned in multiple intercostal or other useful locations.

A further embodiment involves the use of temperature controlled short-term treatments by use of temperature moderated gases. In a further embodiment, the extraction of gases to reduce the support may be performed through the communication lumen. A further embodiment for thermal treatment of the patient involves the therapeutic introduction of thermally adjusted fluids to the bladders. The introduction and removal of the fluids may occur with two ports per bladder to avoid over or under support of the heart.

Similarly, other embodiments, shown in FIGS. 13A-13B, include a perfusion bladder may be included that allows weeping of either a therapeutic or diagnostic agent to the exterior surface of the heart.

This device may be eventually removed by thoracotomy after adequate hemodynamic recovery has been attained. In a further embodiment the device may be of such a profile that it may be introduced via a minimally invasive procedure and delivered and be deployed by trocar or laparoscopic approach. The device may also be explanted by a minimally invasive approach as well.

Figure 14:
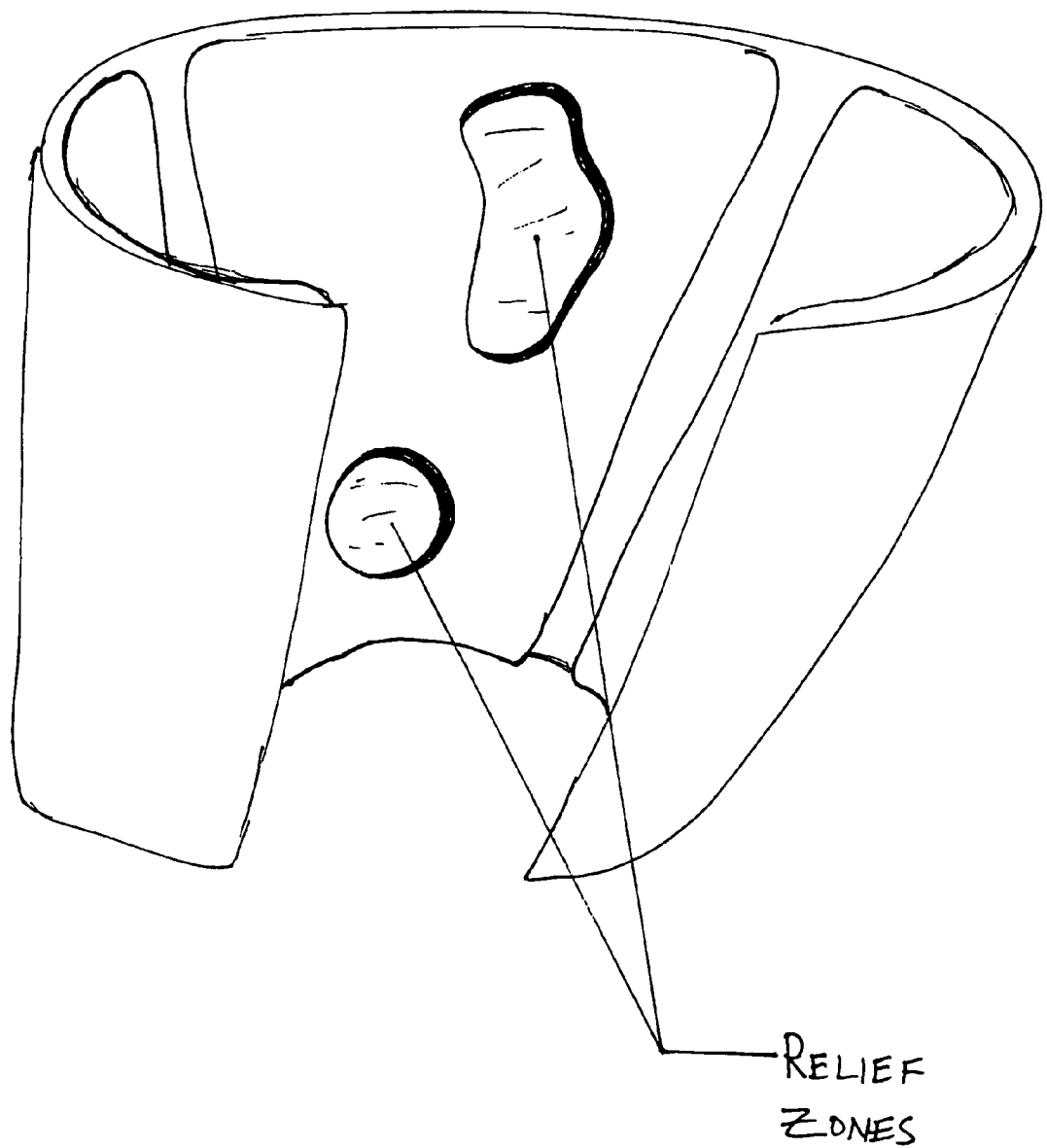
FIG. 14 shows a pair of relief zones that will reduce the pressure components upon localized regions of the heart.

FIG. 14 shows an embodiment of the device with a pair of relief zones that will reduce the pressure components upon localized regions of the heart. These relief zones are placed selectively to minimize the pressure on the heart in desired regions. For instance, in areas that are more susceptible to tissue damage or ischemia due to pressure could be relieved by such zones.

The invention claimed is:

1. A cardiac support apparatus comprising:
   a nonelastic enclosure configured to surround a patient's heart;
   a first inflatable elastic bladder positioned within the enclosure;
   a first subcutaneous injection port having a fluid connection between the subcutaneous injection port and the inflatable elastic bladder; and
   means for therapeutic or diagnostic percutaneous thermal management of the heart;
   whereby a fluid injected into the first subcutaneous injection port inflates the first inflatable elastic bladder to support an epicardial surface of at least one chamber of the patient's heart.

2. The cardiac support apparatus of claim 1, further comprising:
   a second inflatable elastic bladder positioned within the enclosure;
   a second subcutaneous injection port having a fluid connection between the second subcutaneous injection port and the second inflatable elastic bladder.

3. The cardiac support apparatus of claim 2, wherein the first inflatable elastic bladder is configured to support a left ventricle of the patient's heart and the second inflatable elastic bladder is configured to support a right ventricle of the patient's heart.

4. The cardiac support apparatus of claim 3, further comprising:
   a noninflatable LAD relief zone located on one side of the enclosure between the first inflatable elastic bladder and the second inflatable elastic bladder to relieve pressure on the patient's left anterior descending coronary artery; and
   a noninflatable RPD relief zone located on an opposite side of the enclosure between the first inflatable elastic bladder and the second inflatable elastic bladder to relieve pressure on the patient's right posterior descending coronary artery.

5. The cardiac support apparatus of claim 2, further comprising between one and twenty or more bladders and ports to allow for desired positioning and selective support on the heart.

6. The cardiac support apparatus of claim 1, further comprising:
   one or more relief zones in the contact surface of the apparatus to allow less pressure to be placed on desired areas of the heart.

7. The cardiac support apparatus of claim 1, further comprising percutaneous adjustment of said cardiac support apparatus.

8. The cardiac support apparatus of claim 1, wherein said thermal management means includes a thermal agent and wherein said thermal agent is a gas.

9. The cardiac support apparatus of claim 1, wherein said thermal management means includes a thermal mass and wherein said thermal mass is a fluid.

10. The cardiac support apparatus of claim 1, further comprising support means for supporting the heart while protecting the biventricular canal and other coronary vasculature from impingement.

11. A method of delivering the cardiac support apparatus of claim 10, comprising the step of performing a thoracotomy.

12. A method of delivering the cardiac support apparatus of claim 10, comprising the step of performing a minimally invasive procedure.

13. A method of explanting the cardiac support apparatus of claim 10, comprising the step of performing a thoracotomy.

14. A method of explanting the cardiac support apparatus of claim 10, comprising the step of performing a minimally invasive procedure.

15. The cardiac support apparatus of claim 1, further comprising one or more percutaneously adjustable ports for the therapeutic treatment of a failing heart.

16. The cardiac support apparatus of claim 1, further comprising one or more percutaneously adjustable ports for the diagnostic treatment of a failing heart.

17. The cardiac support apparatus of claim 1, wherein said cardiac support apparatus is sized and configured to afford percutaneous access to the exterior of the heart for therapeutic or diagnostic treatment.

18. A method of using the cardiac support apparatus of claim 1, comprising the step of:
   adjusting the cardiac support apparatus through a percutaneously opening in the patient.

19. A method of using the cardiac support apparatus of claim 1 for therapeutic treatment of the recovery of cardiac output, comprising the step of:
   implanting the cardiac support device into a patient with reduced cardiac output.

20. A method of using the cardiac support apparatus of claim 1 for percutaneous thermal management of the heart, comprising the step of:
   implanting the cardiac support device into a patient.

* * * * *